US00PP29579P3

(12) United States Plant Patent
Kolster

(10) Patent No.: US PP29,579 P3
(45) Date of Patent: Aug. 7, 2018

(54) ***HYDRANGEA* PLANT NAMED 'KOLPINBEL'**

(50) Latin Name: *Hydrangea arborescens*
Varietal Denomination: KOLPINBEL

(71) Applicant: Peter Rudolf Kolster, Boskoop (NL)

(72) Inventor: Peter Rudolf Kolster, Boskoop (NL)

(73) Assignee: KOLSTER HOLDING B.V., Boskoop (NL)

( * ) Notice: Subject to any disclaimer, the term of this patent is extended or adjusted under 35 U.S.C. 154(b) by 50 days.

(21) Appl. No.: 15/530,026

(22) Filed: Nov. 21, 2016

(65) Prior Publication Data

US 2017/0172039 P1 Jun. 15, 2017

(30) Foreign Application Priority Data

Dec. 11, 2015 (QZ) ..... PBR 2015/2992

(51) Int. Cl.
*A01H 5/02* (2018.01)

(52) U.S. Cl.
USPC ..... Plt./250

(58) Field of Classification Search
USPC ..... Plt./250
See application file for complete search history.

*Primary Examiner* — Anne Marie Grunberg
(74) *Attorney, Agent, or Firm* — Penny J. Aguirre

(57) ABSTRACT

A new cultivar of *Hydrangea arborescens* plant named 'KOLPINBEL' that is characterized by its strong stems that are held nearly upright, its inflorescences that are light pink in color, and its bloom season that commences early in the season.

2 Drawing Sheets

Botanical classification: *Hydrangea arborescens.*
Varietal denomination: 'KOLPINBEL'.

BACKGROUND OF THE INVENTION

The present invention relates to a new and distinct cultivar of *Hydrangea arborescens* and will be referred to hereafter by its cultivar name, 'KOLPINBEL'. 'KOLPINBEL' represents a new smooth *hydrangea*, a perennial shrub grown for landscape use.

'KOLPINBEL' was derived from an ongoing controlled breeding program directed by the Inventor in Boskoop, the Netherlands. The objective of the breeding program was to develop a new cultivar of *Hydrangea arborescens* with inflorescences that are pink in color on sturdy stems. 'KOLPINBEL' arose from a controlled cross made by the Inventor in Boskoop, The Netherlands in June of 2010 between *Hydrangea* 'NCHA1' (U.S. Plant Pat. No. 20,765) as the female parent and 'Abetwo' (U.S. Plant Pat. No. 20,571) as the male parent. 'KOLPINBEL' was initially selected a single unique plant from amongst the resulting seedlings for further evaluation in 2012 and characteristics confirmed in July of 2014.

Asexual propagation of the new cultivar was first accomplished by stem cuttings by the Inventor in Boskoop, The Netherlands in July of 2012. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'KOLPINBEL' as a unique cultivar of *Hydrangea arborescens.*

1. 'KOLPINBEL' exhibits strong stems t that are held nearly upright.
2. 'KOLPINBEL' exhibits inflorescences that are light pink in color.
3. 'KOLPINBEL' exhibits a bloom season that commences early in the season.

The female parent of 'KOLPINBEL', 'NCHA1' differs from 'KOLPINBEL' in having inflorescences that are deeper pink in color, in having stems that are less strong and held less upright, and in having a shorter plant height. The male parent of 'KOLPINBEL', 'Abetwo', differs from 'KOLPINBEL' in having much larger inflorescences that are white in color and more globular in shape, and in having a taller plant height. 'KOLPINBEL' can be most closely compared to the *Hydrangea arborescens* cultivar 'Pink Pincushion' (not patented). 'Pink Pincushion' is similar to 'KOLPINBEL' in having flower buds that are pink in color. 'Pink Pincushion' differs from 'KOLPINBEL' in having inflorescences that are white in color and comprised of only fertile flowers.

BRIEF DESCRIPTION OF THE DRAWINGS

The accompanying colored photographs illustrate the overall appearance and distinct characteristics of the new *Hydrangea.* The photographs were taken of a plant three years in age as grown outdoors in a trail field in Boskoop, The Netherlands.

The photograph in FIG. 1 provides a view of the plant habit of 'KOLPINBEL' in bloom.

Figure 1:
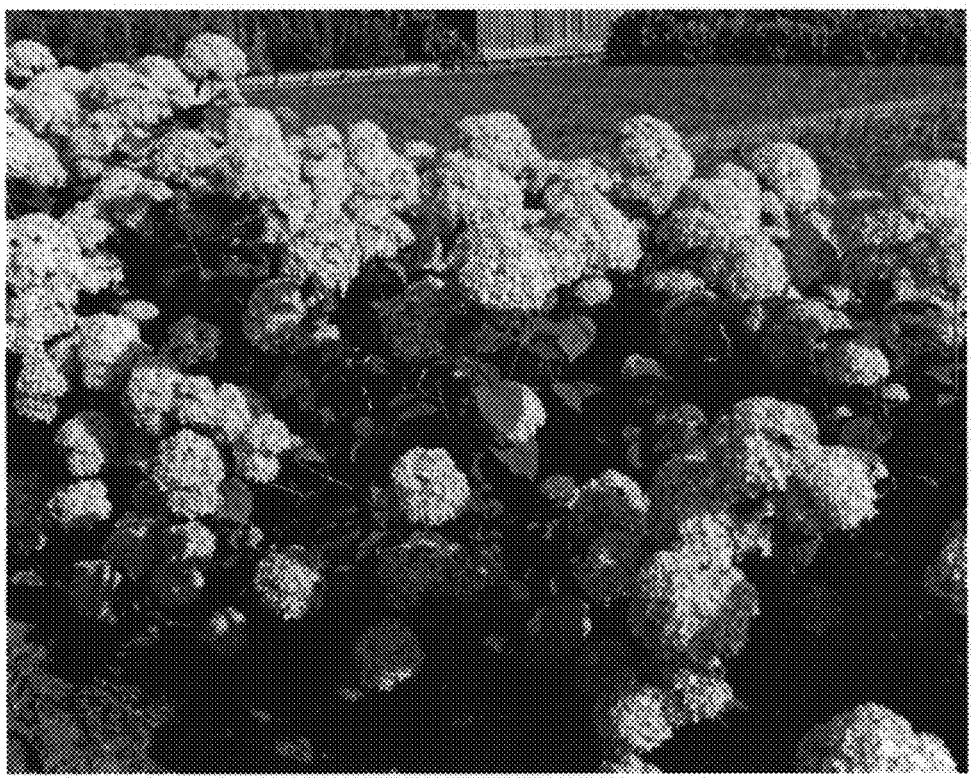
Figure 2:
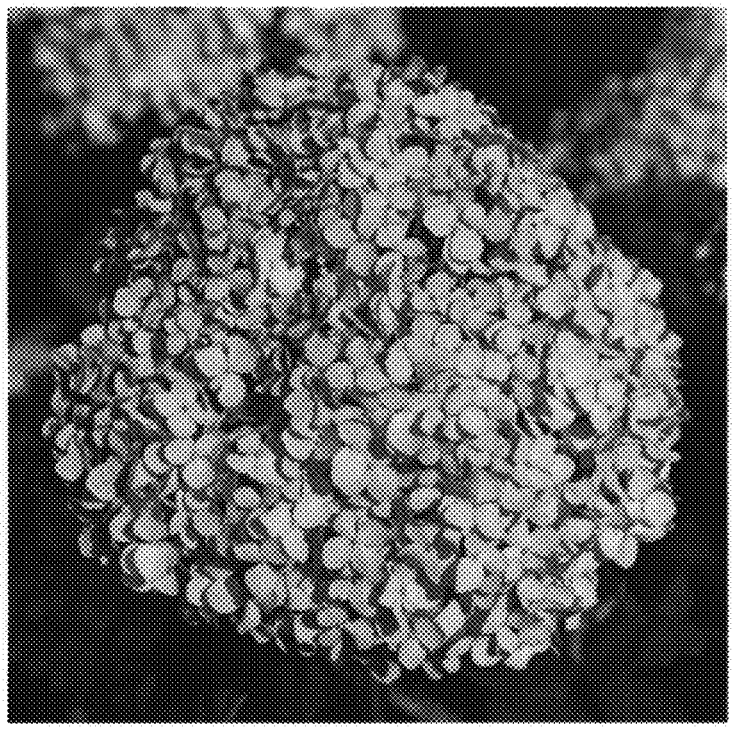

The photograph in FIG. 2 provides a close-up view of an inflorescence of 'KOLPINBEL'.

Figure 3:
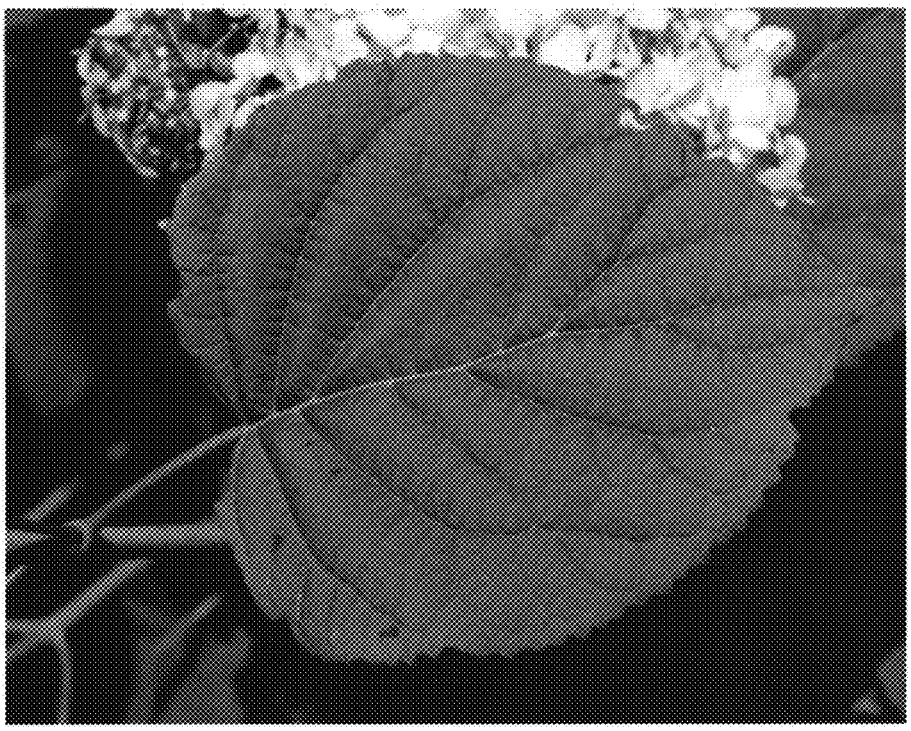

The photograph in FIG. 3 provides a close-up view of a leaf of 'KOLPINBEL'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of plants three years in age as grown outdoors in a trial plot in Boskoop, The Netherlands. The described plant was grown under alkaline soil conditions. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—From July to September in The Netherlands.

*Plant type.*—Perennial shrub, mophead type *hydrangea.*

*Plant habit.*—Broadly spreading to upright with sturdy stems.

*Height and spread.*—An average of 1 m in height and 2.4 m in spread.

*Hardiness.*—At least in U.S.D.A. Zones 5 to 10.

*Diseases and pests.*—No susceptibility and resistance to pests and diseases has been observed.

*Root description.*—Fibrous and fine, 199D in color.

*Propagation.*—Stem cuttings.

*Time required for root development.*—An average of 3.5 weeks for root initiation with a small finished plant produced in about 12 months.

*Growth rate.*—Vigorous.

Stem description:

*Stem shape.*—Rounded.

*Stem strength.*—Strong, do not lodge.

*Stem aspect.*—Upright to an average angle of 60° to soil.

*Stem color.*—Immature stems; 199B to 199C, mature stems; 148D and 144C at the nodes, older bark; 200C.

*Stem size.*—An average of 89.6 cm (excluding the inflorescence) in length and 6 mm in diameter.

*Stem surface.*—Immature and mature stems; glabrous and smooth.

*Branching.*—Freely branched with an average of 80 lateral branches, branching improves with pinching.

*Internode length.*—An average of 12.3 cm.

Foliage description:

*Leaf shape.*—Ovate to broadly ovate.

*Leaf arrangement.*—Opposite.

*Leaf division.*—Simple.

*Leaf number.*—An average of 6 (3 pairs) per lateral branch.

*Leaf base.*—Cordate.

*Leaf apex.*—Apiculate.

*Leaf margins.*—Dentate to serrate.

*Leaf venation.*—Pinnate, upper surface; 146A in color, main vein moderately covered with short adpressed hairs; an average of 0.5 mm in length and 157A in color, lower surface; 146B in color, main and lateral veins densely covered with short hairs; an average of 0.5 mm in length and 157D in color.

*Leaf size.*—An average of 14.5 cm in length and 11 cm in width.

*Leaf attachment.*—Petiolate.

*Leaf surface.*—Upper surface; dull and slightly rugose, lower surface; moderately rugose.

*Leaf color.*—Young leaves; upper surface 146A and lower surface 146B, mature leaves; upper surface; NN137A and lower surface 147B.

*Petioles.*—An average of 5.9 cm in length and 2.5 mm in diameter, color; upper surface 199A and lower surface 151A, upper and lower surfaces; dull and moderately covered with very short, strigose hairs closest to NN155C in color.

Inflorescence description:

*Inflorescence type.*—Globular, mophead, compound corymb of rotate-shaped sterile flowers.

*Lastingness of inflorescence.*—Sterile and fertile flowers; an average of 4 weeks, sterile flowers persistent, fertile flowers self-cleaning.

*Inflorescence number.*—One per lateral stem.

*Inflorescence size.*—An average of 11.8 cm in height and 17.2 cm in diameter.

*Flower number.*—An average of 800 sterile flowers and 480 fertile flower buds per inflorescence.

*Flower fragrance.*—None.

*Flower aspect.*—Sterile flowers; upright, outwards and slightly drooping, fertile flowers; upright.

*Flower size.*—Sterile flowers; an average of 1.6 cm in diameter and 4 mm in depth, fertile flowers; an average of 1 mm in diameter and 1.5 mm in depth.

*Flower shape.*—Sterile flowers; rotate, fertile flowers; do not open, remain in the bud stage.

*Flower buds.*—Sterile flowers; an average of 2.5 mm in length and 2 mm in diameter, obovate in shape, 59B in color, fertile flowers; an average of 2 mm in length and 1.75 mm in diameter, obovate in shape, 195C suffused with 59B at the apex and 146D at the base.

*Peduncles.*—An average of 17 cm in length and 5 mm in diameter, held upright, 148D suffused with 199C in color, smooth surface.

*Pedicels.*—Sterile flowers; an average of 9 mm in length and 1 mm in diameter, held at an average angle of 45° to vertical, 176B in color, moderate strength, moderately covered with thin hairs an average of 0.5 mm in length and NN155A in color, fertile flowers; an average of 2 mm in length and 0.75 mm in diameter, held at an average angle of 15° to vertical, 151A in color, moderate strength, dull surface moderately covered with thin hairs an average of 0.5 mm in length and NN155A in color.

*Petals.*—Sterile flowers; about 4 to 5, do not open (form petal center spot), ovate in shape, acute apex, cuneate base, entire margin, an average of 1 mm in length and 1.25 mm in width, color; upper surface 155A and lower surface 185D, color does not fade, glabrous and dull upper and lower surfaces, fertile flowers; 4 to 5, do not open, stay in the bud phase, ovate in shape, acute apex, cuneate base, entire margin, an average of 1 mm in length and 0.75 mm in width, color; upper and lower surfaces 195C suffused with 59B at the apex, both surface glabrous and dull.

*Sepals.*—Sterile flowers; an average of 4, rotate in arrangement, broad ovate in shape, very slightly concave, very short apiculate apex, cuneate base, entire margin, an average of 7 mm in length and 6 mm in width, color; upper surface when opening 185D, lower surface when opening 58A, upper surface when fully open a blend between 65C and 186D, lower surface when fully open 186B, color does not fade, both surfaces; glabrous, smooth, and dull, fertile flowers; an average of 5, rotate in arrangement, ovate to deltoid in shape, acute apex, broadly cuneate base, entire margin, an average of 0.2 mm in length and 0.5 mm in width, color; upper and lower surfaces when opening and upper surface when fully open 150B, lower surface when fully open 176B, color does not fade, both surfaces glabrous and dull.

Reproductive organs:

*Gynoecium.*—Sterile; none observed, fertile flowers; not developed and covered by petals closed into buds that do not open, ovary 150B in color.

*Androecium.*—Sterile; none observed, fertile flowers; not developed and covered by petals closed into buds that do not open.

*Fruit and seed.*—No seeds or fruit observed to date.

It is claimed:

1. A new and distinct cultivar of *Hydrangea* plant named 'KOLPINBEL' substantially as herein illustrated and described.

* * * * *